US00PP19076P2

(12) United States Plant Patent
Utecht

(10) Patent No.: US PP19,076 P2
(45) Date of Patent: Aug. 5, 2008

(54) ***PELARGONIUM* PLANT NAMED 'FISROLAMON'**

(50) Latin Name: *Pelargonium×hortorum*
Varietal Denomination: Fisrolamon

(76) Inventor: Angelika Utecht, Hinterer Rebstock 38, Montabaur (DE), 56410

( * ) Notice: Subject to any disclaimer, the term of this patent is extended or adjusted under 35 U.S.C. 154(b) by 0 days.

(21) Appl. No.: 11/803,253

(22) Filed: May 14, 2007

(51) Int. Cl.
*A01H 5/00* (2006.01)

(52) U.S. Cl. ..... Plt./327; Plt./325

(58) Field of Classification Search ..... Plt./327, Plt./325

See application file for complete search history.

*Primary Examiner*—Kent L. Bell
*Assistant Examiner*—S. B. McCormick-Ewoldt
(74) *Attorney, Agent, or Firm*—Jondle & Associates, P.C.

(57) ABSTRACT

A new cultivar of *Pelargonium* particularly characterized by having deep salmon-orange, round, open and semi-double flowers, large umbels borne well-above the foliage, medium-green foliage with medium to strong zonation, a moderately vigorous growth habit and a well-branched and relatively tall plant habit, is disclosed.

1 Drawing Sheet

Genus and species: *Pelargonium×hortorum.*
Variety denomination: 'Fisrolamon'.

BACKGROUND OF THE NEW PLANT

The present invention comprises a new and distinct cultivar of *Pelargonium,* botanically known as *Pelargonium×hortorum,* and hereinafter referred to by the cultivar name 'Fisrolamon'. The new cultivar is a product of a planned breeding program which had the objective of creating new varieties having pink flowers, good flower color stability, medium-green foliage and vigorous growth. 'Fisrolamon' was discovered as a seedling resulting from a cross between the female parent 'Fishelen' (U.S. Plant Pat. No. 12,727), a *pelargonium* plant having salmon-pink flowers and the male parent, 'Fisorange' (U.S. Plant Pat. No. 12,485), a *pelargonium* plant having deep salmon-orange flowers. A single plant selection was chosen for further evaluation and for asexual propagation in 2003.

The new cultivar was created in 2002 in Hillscheid, Germany and has been asexually reproduced repeatedly by vegetative cuttings in Galdar, Gran Canaria, Spain, and Hillscheid, Germany over a 4-year period. 'Fisrolamon' has not been observed under all possible environmental conditions, thus, the phenotype may vary significantly with variations in the environment such as temperature, light intensity and day length. It has been found to retain its distinctive characteristics through successive asexual propagations.

Plant Breeder's Rights for this cultivar were applied for in Germany on Apr. 25, 2006 and in Canada on Apr. 26, 2006.

SUMMARY OF THE INVENTION

The following are the most outstanding and distinguishing characteristics of this new cultivar when grown under normal commercial practices in Hillscheid, Germany.

1. A deep salmon-orange flower color with wide open, semi-double flowers;
2. Large inflorescences borne well-above the foliage;
3. Medium-green foliage with medium to strong zonation;

4. A moderately vigorous growth;
5. A rounded plant habit with good branching; and
6. An early to medium spring flowering response.

DESCRIPTION OF THE PHOTOGRAPH

This new *pelargonium* plant is illustrated by the accompanying photograph which shows blooms, buds, and foliage of the plant; the colors shown are as true as can be reasonably obtained by conventional photographic procedures. The photograph is of three plants in a tube about 6 and one-half-months old and grown from rooted cuttings in a 14-cm pot under greenhouse conditions which approximate those generally used in commercial practice.

DESCRIPTION OF THE NEW CULTIVAR

The following detailed descriptions set forth the distinctive characteristics of 'Fisrolamon'. The data which define these characteristics were collected from asexual reproductions carried out in Hillscheid, Germany. The plant history was taken on 10-week-old, un-pinched plants in 12-cm pots in a greenhouse in mid-May 2006. The color readings were determined under natural light in mid-May from flowers grown in a greenhouse. Color references are to the R.H.S. Colour Chart of The Royal Horticultural Society of London (R.H.S.) (2001).

DETAILED BOTANICAL DESCRIPTION

Classification:
*Botanical.*—*Pelargonium×hortorum* Bailey.
*Common name.*—Zonal geranium.

Parentage:
*Female parent.*—'Fishelen' (U.S. Plant Pat. No. 12,727) a *pelargonium* plant having salmon-pink flowers.
*Male parent.*—'Fisorange' (U.S. Plant Pat. No. 12,485) a *pelargonium* having deep salmon-orange flowers.

Plant:
*Form.*—Shrub, self-branching, rounded shape.
*Branching habit.*—6.0 branches on average per plant.

*Height.*—11.1 cm for a 10-week-old plant (measured from base of stem to the tips of the branches, excluding the inflorescences).

*Width.*—26.8 cm for a 10-week-old plant.

*Time to produce a finished flowering plant.*—For the spring flowering response in Hillscheid, Germany, in 2006, about 7 weeks after planting of rooted cuttings, 50% of the plants were flowering with at least one open flower on Apr. 28, 2006.

*Outdoor plant performance.*—Plants continuously flower, a flower count in mid-September of 2006 in Hillscheid, Germany indicated about 13–16 inflorescences per plant.

Leaves:

*Arrangement.*—Alternate, at flowering stems opposite.

*Color, Immature leaf.*—General: Grass-green. Upper surface: RHS 143A. Lower surface: RHS 143B.

*Color, mature leaf.*—Upper surface: RHS 137C to RHS 137D. Lower surface: Between RHS 143A and RHS 144A.

*Length.*—5.5 cm to 6.0 cm.

*Width.*—9.2 cm.

*Zonation color.*—RHS 200C (brown) with a relatively strong distinctness.

*Zonation diameter.*—Inner diameter of the ring is 5.1 cm, the band or belt of zonation is about 2.0 cm to 2.5 cm wide.

*Shape.*—Kidney-shaped to round with weak lobes and an open gap between the lowest lobes.

*Apex.*—Rounded.

*Base.*—Cordate.

*Margin.*—Bi-crenate and wavy.

*Texture.*—Upper surface is dull and velvety.

*Leaf veins.*—Protruding on the lower surface and are RHS 144B.

Petioles:

*Length.*—About 5.0 cm to 8.0 cm.

*Diameter.*—0.3 cm.

*Color.*—RHS 144B (light yellow-green).

*Texture.*—Covered with fine pubescence.

Stems:

*Length.*—7.0 cm to 9.0 cm.

*Internode length.*—1.0 cm to 3.0 cm.

*Color.*—RHS 143C (light-green).

*Texture.*—Appears smooth, yet covered with very short pubescence.

Flower buds (just before petals unfold):

*Length.*—1.6 cm.

*Width.*—0.9 cm.

*Shape.*—Elliptical, relatively narrow.

*Color of sepals.*—RHS 143B (light-green).

*Color of petals.*—RHS 41A to RHS 41B (orange-red).

Inflorescence:

*Type.*—An umbel composed of roughly 20 to 40 flowers and buds.

*Umbel diameter.*—11.2 cm.

*Umbel depth* (*Height*).—5.5 cm to 6.0 cm.

*Umbel shape.*—Nearly semi-spherical.

*Lastingness of umbel on the plant.*—About 16 to 18 days.

*Peduncle.*—Length: 15.5 cm. Diameter: 0.5 cm. Texture: Densely pubescent with short glandular hair. Color: RHS 143 B (light-green).

*Pedicel.*—Length: 2.9 cm. Diameter: 0.15 cm. Texture: Covered with short glandular hair. Color: Mainly RHS 144A (light-green) and RHS 181A (reddish) at the flower end.

Corolla:

*Diameter.*—5.3 cm.

*Depth.*—1.3 cm to 1.5 cm.

*Form.*—Semi-double.

*Shape.*—Round outline; the upper petals and lower petals are roughly of the same size, wide open and saucer-shaped.

*Number of petals.*—6 to 8.

*Petaloids.*—May occur. Number: 0 to 2. Shape: variable; shorter and narrower than the petals and often folded or somewhat twisted. Color: Approximately RHS 41A to RHS 41B.

*Lastingness of the individual flowers on the plant.*—6 to 8 days at 18° C.

*Fragrance.*—The umbels are not fragrant but the peduncles, pedicels and sepals when touched, give off an aromatic scent (typical for *Pelargonium zonale* or *Pelargonium×hortorum* varieties).

Petals:

*Color.*—In general, light orange-red to deep salmon.

*Upper petals.*—Length: 2.7 cm. Width: 1.9 cm to 2.2 cm. Color: Upper surface: Mainly RHS 40A to RHS 41A and partly RHS 43B to RHS 43C. Lower surface: Marbled RHS 41B to RHS 43C. Markings: Slight fading of color at base of RHS 43C and weak to hardly visible veins of RHS 43A to RHS 43B.

*Lower petals.*—Length: 2.6 cm. Width: About 2.2 cm to 2.3 cm. Color: Upper surface: RHS 40B to RHS 43B and may turn to pink or fade somewhat from RHS 43C to RHS 50B, especially when outdoors. Lower surface: Between RHS 41B and RHS 43C, somewhat variable. Markings: None.

*Shape.*—Obovate.

*Apex.*—Rounded.

*Base.*—Broadly acute.

*Margin.*—Entire.

*Texture.*—Smooth, slightly glossy.

Sepals:

*Number.*—5.

*Length.*—1.0 cm to 1.1 cm.

*Width.*—0.4 cm for the largest upper sepal and 0.3 cm for the other sepals.

*Shape.*—Lanceolate.

*Apex.*—Acute.

*Base.*—Fused.

*Margin.*—Entire.

*Texture.*—Short glandular hair and a few longer hairs.

*Color.*—Upper (outer) surface: Mainly RHS 144A (light-green) and RHS 181A near the base. Lower (inner) surface: RHS 144B.

Reproductive organs:

*Androecium.*—Number of anthers: Most often 7. Filament color: Mainly RHS 155A (white) to RHS 49B at the upper end. Filament length: 0.7 cm. Pollen color: RHS 24A (orange). Pollen amount: Moderate (typical).

*Gynoecium.*—Pistil number: 1. Pistil length: 0.8 cm to 0.9 cm. Stigma color: RHS 46B to RHS 53B (deep-red). Stigma shape: 5 to 6 lobed. Style color: RHS 45C. Style length: 0.6 cm to 0.7 cm. Style shape: Filiform (filament-like) with the lobes of the stigma at right angles.

Fruit/seed set: A few seeds are developed, most often in late summer to fall. The fruit are ovate, 0.8 cm in length and have a total length of 3.3 cm (including the 'beak'). The seeds are fertile.

Disease and insect resistance: No special observations made, average susceptibility or tolerance; not resistant to diseases and pests common to the species.

COMPARISON WITH PARENTAL AND COMMERCIAL CULTIVARS

'Fisrolamon' differs from the female parent 'Fishelen' (U.S. Plant Pat. No. 12,727) in that 'Fisrolamon' has a deeper salmon-orange flower color outdoors and a taller plant habit outdoors than 'Fishelen'.

'Fisrolamon' differs from the male (pollen) parent 'Fisorange' (U.S. Plant Pat. No. 12,485) in that 'Fisrolamon' has larger flowers and inflorescences with longer peduncles and a taller plant habit than 'Fisorange'.

'Fisrolamon' differ from the commercial comparison variety 'Fisroccal' (U.S. Plant Pat. No. 16,933) in that 'Fisrolamon' has a deeper overall flower color, smaller foliage with more distinct leaf zonation and an earlier spring flowering response than 'Fisroccal'.

'Fisrolamon' differs from the commercial comparison variety 'Americana Coral' (U.S. Plant Pat. No. 7,934) in that 'Fisrolamon' has a lighter overall flower color but more distinct zonation of the leaves, while 'Americana Coral' develops nearly no zonation.

I claim:

1. A new and distinct cultivar of *Pelargonium* plant as shown and described herein.

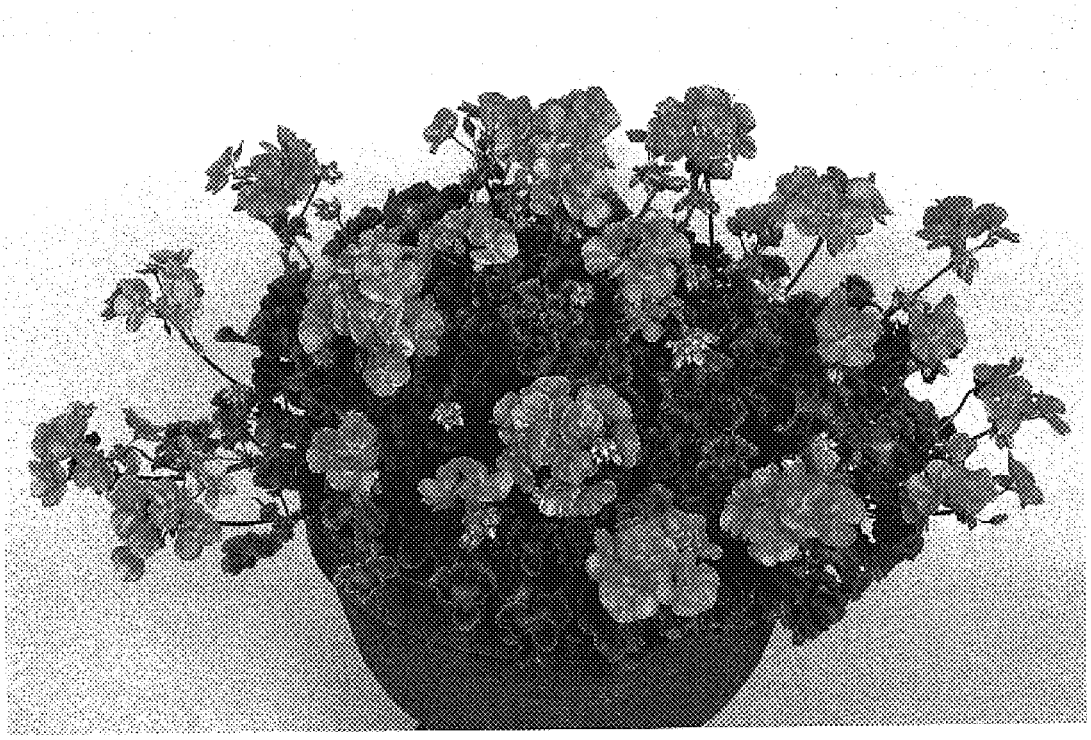

* * * * *